United States Patent [19]

Hochberg et al.

[11] Patent Number: 4,658,825
[45] Date of Patent: Apr. 21, 1987

[54] SPIRAL PROBE FOR SIMULTANEOUS ELECTRICAL AND CHEMICAL MONITORING OF A FETUS

[75] Inventors: Howard M. Hochberg, Woodinville, Wash.; Edwin L. Schmalzbach, Roosevelt; Janis G. Ziedonis, West Windsor, both of N.J.

[73] Assignee: International Biomedics, Inc., Bothell, Wash.

[21] Appl. No.: 832,529

[22] Filed: Feb. 24, 1986

Related U.S. Application Data

[63] Continuation of Ser. No. 616,440, May 31, 1984, abandoned, which is a continuation-in-part of Ser. No. 425,036, Sep. 24, 1982, abandoned.

[51] Int. Cl.[4] ............................. A61B 5/00; A61B 5/04
[52] U.S. Cl. ...................................... 128/634; 128/642
[58] Field of Search ....................... 128/634, 635, 642

[56] References Cited

U.S. PATENT DOCUMENTS

| | | | |
|---|---|---|---|
| 4,200,110 | 4/1980 | Peterson et al. | 128/634 |
| 4,244,375 | 1/1981 | Farrar et al. | 128/642 |
| 4,281,659 | 8/1981 | Farrar et al. | 128/642 |
| 4,294,258 | 10/1981 | Bernard | 128/642 |
| 4,321,931 | 3/1982 | Hon | 128/642 |

FOREIGN PATENT DOCUMENTS 7419624  9/1974  Fed. Rep. of Germany ...... 128/642

OTHER PUBLICATIONS

Aarnoudse et al, "Fetal . . . $PO_2$ and Abnormal Heart Rate During Labor", Am. J. Ob. & Gyn., vol. 158, No. 5, Nov. 1985.

*Primary Examiner*—Lee S. Cohen
*Attorney, Agent, or Firm*—Jensen & Puntigam

[57] ABSTRACT

A combined spiral EKG electrode and pH probe for use in monitoring a fetus during labor is described. The combined probe includes a spiral-shaped needle which acts as an EKG electrode and also houses a fiberoptic pH probe. Optical fibers and wires from the needle as well as from a reference electrode on the probe assembly are passed back through the cervix and vagina of a woman in order to provide simultaneous information as to both EKG and pH of the fetus during labor.

3 Claims, 8 Drawing Figures

SPIRAL PROBE FOR SIMULTANEOUS ELECTRICAL AND CHEMICAL MONITORING OF A FETUS

This is a continuation of application Ser. No. 616,440, filed on May 31, 1984, now abandoned, which in turn is a continuation-in-part of Ser. No. 425,036, filed on Sept. 24, 1982 (now abandoned).

DESCRIPTION

1. Technical Field

The present invention relates generally to apparatus for fetal monitoring, and more particularly concerns a sensor for continuously measuring both fetal EKG (electrocardiogram) signals and fetal pH (hydrogen ion concentration) during labor and delivery.

2. Background Art

Heretofore, a variety of probe or electrode structures and applicators therefor have been designed for insertion through the vagina and cervix of a woman in labor and attachment to the epidermis of a fetus. It is well known to obtain a fetal EKG by this method. Such probe structures are designed to be operatively connected to an amplifier and a cardiotachometer for recording the fetal electro-cardiogram and heart rate during the labor and delivery process. One such device is described in U.S. Pat. No. 4,321,931, issued to E. D. Hon on Mar. 30, 1982. The apparatus disclosed therein consists of a single small helix-shaped electrode which is rotated or screwed into the skin of the head of the fetus. The reference lead is external of the fetus, in contact with the tissue of the mother. Such apparatus is well known and accepted in the medical profession. It should be noted that only a contact is necessary to obtain good results. Fixation of the electrode, or penetration to a particular region of the scalp, is not necessary.

However, such apparatus records only electrical impulses related to the fetal heart rate, i.e. an EKG. It is also desirable that certain chemical conditions of the fetus, specifically the pH value of the blood, be continuously monitored during the labor and delivery process, and it would be highly desirable to combine pH and EKG functions in a single probe which is as simple to use and as conventional in appearance and use as is the known EKG probe discussed above. However, accurate pH readings require a stable, i.e. essentially motionless, positioning of the needle after insertion, and penetration of the needle to a particular tissue region beneath the skin.

The pH monitoring is important because pH is related largely to the carbon-dioxide and acid concentration in the blood, and thus it is recognized that the pH value of the blood (or tissue) of a fetus during delivery will usually provide an early indication of fetal distress, since increased carbon dioxide, with or without fixed acid concentration, as manifested by decreasing pH values, will usually mean that the fetus is receiving insufficient oxygen, due to a compression of the umbilical cord or other reasons. Continuation of a condition of insufficient oxygen will result in permanent brain damage to the fetus.

Various pH electrodes have heretofore been developed for the purpose of continuously monitoring the pH values of a fetus, typically by attachment to the scalp of the fetus. Such electrodes have used two electro-chemical half-cells with the potentials across the half-cells connected in opposition, which normally results in a cancellation of the two potentials. Various types of conventional ion selective glass electrodes are described in U.S. Pat. No. 3,959,107 to Horner and U.S. Pat. No. 3,973,555 to Moller et al. A spiral-type apparatus is described in U.S. Pat. No. 4,320,764 to Hon. A further device is shown in U.S. Pat. No. 3,224,433 to Dalebor, cited in the above-identified parent application. However, such electrodes have either been unpractical or did not operate well and hence have not been successfully commercialized.

In a related development, as shown in U.S. Pat. No. 4,220,110 to Peterson, et al, a fiber optic pH probe suitable for implantation in tissue for physiological studies is described. The probe described by Peterson et al includes an ion permeable membrane envelope which encloses the ends of a pair of optical fibers. A pH sensitive dye indicator composition is present within the envelope. The probe operates on the concept of optically detecting changes in the color of the pH sensitive dye. Such an apparatus does not require an external reference and typically requires only a single small rod or needle-like electrode through which the fibers pass. Such devices have proven to be electrically safe, and substantially drift free for extended periods of time.

As noted above, monitoring of both the fetal heart rate and the pH of the fetus are desirable. Also, as indicated above, separate electrode sensors have been developed to monitor the fetal heart rate and the pH of a fetus, respectively. Attachment of two separate probes to the fetus, however, significantly increases the trauma to the skin, and is therefore undesirable. Further, the pH probe must be maintained in a stable position on the fetus, so that the needle does not move following insertion, or inaccurate readings will result. Still further, the pH probe must penetrate the skin layer, instead of just contacting the skin. The penetration must be below the skin, to measure the interstitial fluid.

Accordingly, prior pH probes have used rather elaborate attachment devices in an attempt to insure stable positioning and accurate penetration relative to the scalp of the fetus, the difficulty of which is increased because the device must be inserted through the vagina and cervix of a woman in labor. U.S. Pat. No. 4,294,258 to Bernard shows a combined EKG and pH probe which includes multiple retracting claws or opposing helixes in an attempt to provide the required stability. Bernard specifically teaches that such structure is necessary to maintain the combined probe in place. The '931 patent to Hon, supra, teaches the use of a needle which is driven through the skin of the fetus by a spiral which in turn is threaded into the skin by hand or by a special tool. Neither structure has proven to be practical in actual use.

It is thus desirable to have a simple and practical combined EKG and pH probe which incorporates the familiar single spiral form of existing EKG electrodes and causes minimum trauma to the fetus, but which maintains a sufficiently stable position on the fetus to provide good pH readings during the labor and delivery process. As noted above, during the labor and delivery process, the fetus is constantly moving and twisting, as is the mother, which results in conventional probes, even those shown in Bernard, moving or even being dislodged. The movement of the pH sensor results in inaccurate readings of pH, and further causes trauma to the fetus where the probe is attached. These problems have been recognized in the art for some time and have been considered to be very significant. However, the art has heretofore been unsuccessful in solving these problems, and it is not apparent how they could be solved with a single spiral needle, which is a preferred arrangement, as explained above.

DISCLOSURE OF THE INVENTION

Accordingly, the present invention is a spiral probe capable of simultaneous and continuous electrical and chemical monitoring of a fetus. The invention includes a low profile, low height base element which is relatively wide compared to its height and at least one electrically conductive spiral-shaped needle element which extends from the base and is adapted to be inserted into the scalp of the fetus. The base element includes a reference electrical electrode. Fiberoptic means extend through the needle element for detection of a selected chemical in the scalp tissue of the fetus. Such a probe, once inserted, remains in stable position, essentially without moving, on the scalp of the fetus during labor of the mother and delivery of the fetus.

BEST MODE FOR CARRYING OUT THE INVENTION

Figure 1:
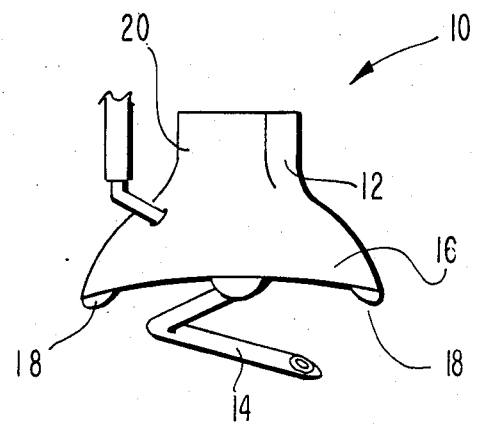
FIG. 1 is an elevational view of the combined EKG and pH probe of one embodiment of the present invention.
Figure 2:
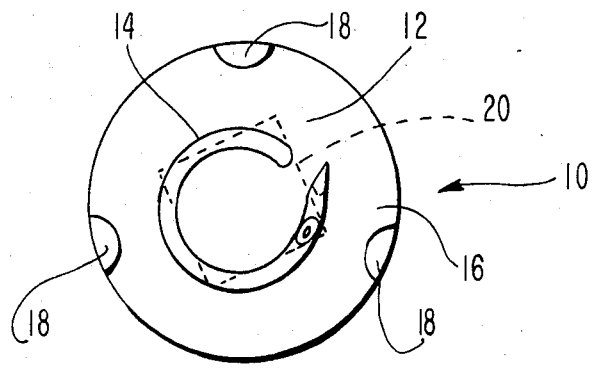
FIG. 2 is a bottom plan view of the probe of FIG. 1.
Figure 3:
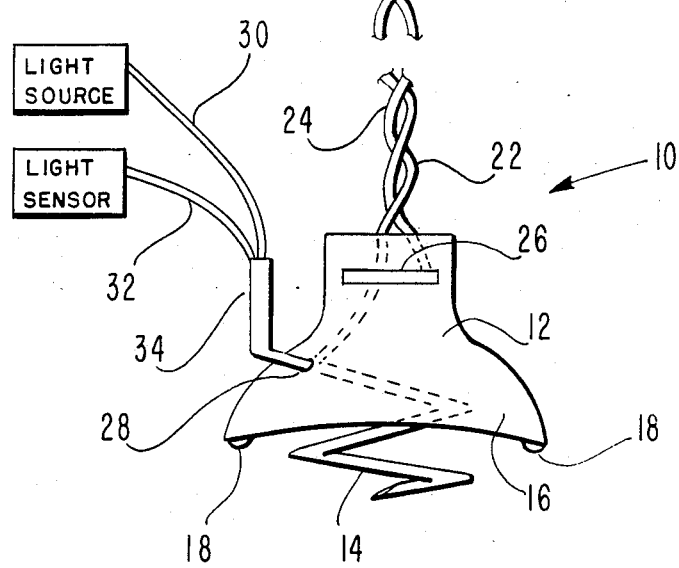
FIG. 3 is a cross-sectional elevational view of the probe of FIG. 1.

Referring generally to FIGS. 1-3, one embodiment of the combined EKG and pH probe 10 of the present invention is shown. The probe 10 is comprised of a base assembly 12 which is made of a soft material such as a silicone plastic. Molded into the plastic base 12 is a hollow, electrically conductive, spiral-shaped needle 14. The needle 14 is used both as the EKG electrode and also as a housing for a fiber optic probe for monitoring of pH. The needle 14 extends out of the broad portion 16 of the base assembly 12. The broad portion 16 of the base assembly 12 is somewhat concave and has raised bumps 18 formed thereon. The base assembly 12 tapers from the broad portion 16 to a top 20 which is substantially squared in shape (when viewed from the end) in order that a square tube (not shown) can be used as an applicator for inserting the electrode 10 into the scalp of the fetus through the vagina and cervix of a woman in labor. A pair of wires 22, 24 are electrically connected to the hollow, spiral needle 14 and to a reference electrode 26 formed at the top 20 of the plastic base assembly 12. The hollow neede 14 extends through the side 28 of the base assembly 12 in order to permit optical fibers 30, 32 to pass down through a tube 34 into the end of the needle 14.

Figure 4:
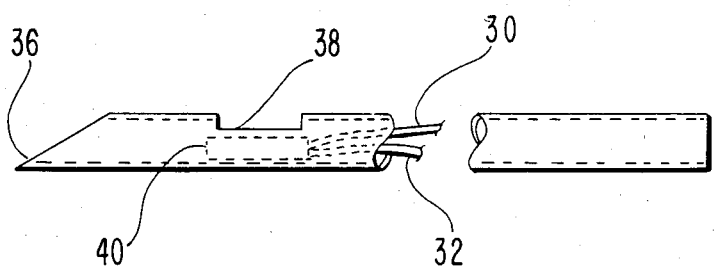
FIG. 4 is an exploded view of one embodiment of the end of the needle portion of the present invention.

Referring now to FIG. 4, the end of the needle 14 comes to a point 36. Near the point 36 of the needle 14 is a window 38 formed in the needle 14 in order to allow body fluids from the scalp of the fetus to enter into the area containing the fiber optic probe 40 and ion permeable membrane envelope. These items operate in a manner more fully described in U.S. Pat. No. 4,200,110, supra.

Figure 5:
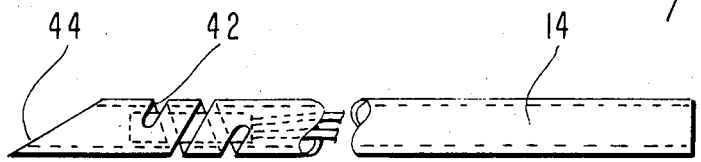
FIG. 5 is another embodiment of the subject matter of FIG. 4.

Referring to FIG. 5, an alternative embodiment of the end portion of the needle is shown. In the alternative embodiment there is a spiral opening 42 cut adjacent the end 44 of the needle 14 to permit body fluids from the scalp of the fetus to enter the ion permeable membrane of the fiber optic pH probe.

The purpose of the squared off top end 20 of the plastic base assembly 12 is to permit the use of an elongated tube (not shown), which is typically constructed of plastic, and which also has a squared off end, to be used as an insertion tool for applying the probe 10 through the vagina and cervix of a woman in labor and into the scalp of a fetus.

Figure 6:
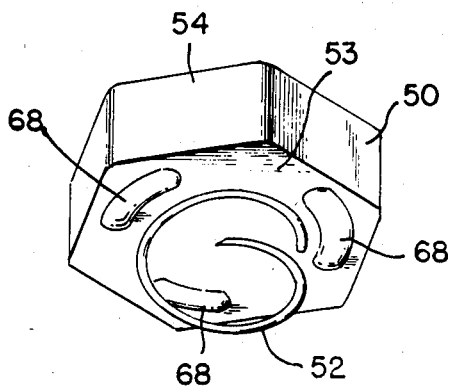
FIGS. 6 thru 8 show a further embodiment of the combined pH and EKG probe of the present invention.
Figure 7:
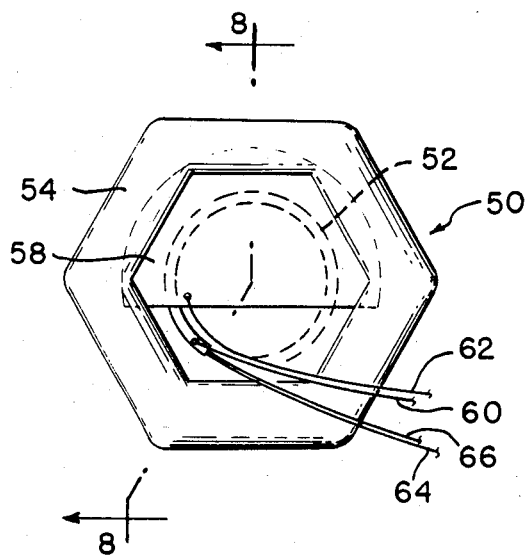
Figure 8:
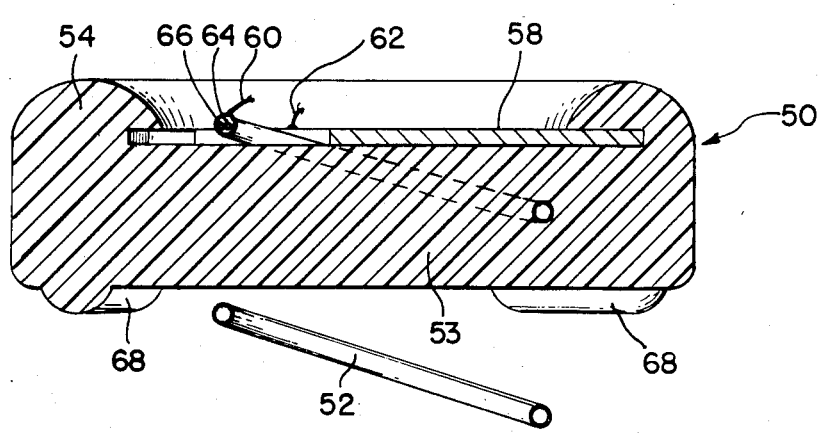

FIGS. 6-8 show a further embodiment of the present invention. A low profile base 50 includes, as with the other embodiments described above, a single spiral needle 52, one end of which is molded into base 50, and the other end of which extends outwardly from the bottom of base 50 in a spiral. The spiral needle 52 is hollow, so that it may be used simultaneously as an EKG electrode, and as a housing for the fiber optic probe for the pH monitoring. It should be understood, however, that two spirals could be used, one for EKG and the other for pH.

In the embodiment shown, the base 50 is formed of plastic, and is approximately two centimeters across, substantially wider than conventional probes. It is hexagonal in outline, approximately 1 centimeter on a side. Referring now to the drawings more specifically, the base 50 comprises a thin flat central portion 53 bounded by a surrounding wall portion 54, thereby defining a central cavity in the base. The wall portion 54 is rounded at its top edges and at each corner and is approximately 0.5 centimeters (5 millimeters) high, which results in a low-profile base which is quite wide relative to its height and which is unlikely to dislodge by virtue of contact with the mother's tissue.

Spaced over a substantial portion of the central cavity in the base but slightly below the top edge of wall portion 54 is a thin flat metal plate 58 which functions as a reference electrode for the EKG probe. Electrical leads 60 and 62 are connected, respectively, to needle 52 and plate 58, while conventional optical fibers 64 and 66 extend down through the center of the needle to near the end thereof, where it terminates in a dye-containing membrane, adjacent a window in the needle, as described above with respect to the other embodiment. Needle 52 is sharply pointed at its end so that it can easily penetrate the scalp of the fetus. In the embodiment shown, needle 52 has a spiral diameter of approximately 1 centimeter and provides 5.2 mm ±0.3 mm of penetration, in approximately 1½ turns.

On the lower surface of base 50 are molded 3 elongated humps 68—68 which in the embodiment shown are spaced equally apart and are approximately 4-6 millimeters long, approximately 2-3 millimeters wide and approximately 1 millimeter high. The humps aid in the stable positioning of the probe after it has been attached to the fetus and help to prevent the probe from backing out after attachment. Since base 50 is hexagonal, the combined probe may be easily applied by hand or by a special tool (not shown) to the scalp of the fetus. Twisting of the probe positions the probe securely into the scalp of the fetus. After proper insertion, the tip of the probe is in the desired area, beneath the skin layer. Once inserted, the probe will not move, so that accurate pH readings are obtained. Lack of movement also significantly reduces the trauma to the fetus. The EKG readings are of course accurate since only a skin contact is necessary. The combination of the relatively wide dimension base, which has a relatively low profile and rounded corners, with a single spiral needle results in a stable probe which remains positioned without substantial movement on the fetus during labor and delivery, and thus provides both reliable EKG and pH data. Such a probe is also simple to apply and use, as well as being practical in operation, and causes a minimum trauma to the tissue of the fetus.

In summary, the embodiment of FIGS. 6-8, as well as the other embodiments disclosed herein, provide simultaneous monitoring of both EKG and pH of a fetus during labor through use of a single spiral needle probe which is inserted into the scalp of the fetus. Thus, the benefits derived from both EKG monitoring and pH monitoring are simultaneously and continuously available in a relatively simple, practical design.

Although a preferred embodiment of the invention has been disclosed herein for illustration, it should be understood that various changes, modifications and substitutions may be incorporated in such embodiment without departing from the spirit of the invention as defined by the claims which follow.

We claim:

1. A unitary probe for simultaneous electrical and chemical monitoring of a fetus, comprising:
    a low profile, low height probe body, said probe body being relatively wide compared to its height;
    a single, electrically conductive, spiral-shaped hollow needle element, having more than one complete turn, which is integral with said probe body and extends downwardly from said probe body a particular distance such that when the probe is operatively positioned on the scalp of the fetus, the tip of said needle element thereof extends a controlled depth into the tissue of the fetal scalp beneath the skin for monitoring of the pH of the fetus, wherein the dimensions and configuration of the needle element are such, in combination with the low height of the probe body, that the probe remains relatively stable on the fetal scalp during labor of the mother and delivery of the fetus such that accurate chemical as well as electrical monitoring of the fetus is accomplished;
    fiberoptic probe means adapted to extend through said needle element, including means for detecting a selected chemical condition, such as pH, in the scalp tissue of the fetus;
    a reference electrode in said probe body; and
    means for electrically connecting said needle element and said reference electrode to a selected electrical monitoring apparatus, such that a desired electrical monitoring procedure, such as an EKG, can be accomplished.

2. An apparatus of claim 1, wherein the width of said probe body at its lower surface is approximately at least four times as great as the height of said probe body, wherein the outer peripheral surface of said probe body extends substantially vertically upwardly from its lower surface and then curves inwardly to a point of maximum height for said probe body, and wherein the outer peripheral surface of said probe body comprises a succession of substantially flat surfaces around the periphery of said probe body, the flat surfaces being rounded where they mate with adjacent flat surfaces, the configuration of the outer peripheral surface of said probe body facilitating the positioning of the unitary probe onto the scalp of a fetus.

3. An apparatus of claim 2, wherein said probe body is approximately 2 cm wide and 5 mm high, wherein the needle element is molded into said probe body and wherein said needle element has a spiral of approximately 1½ turns, extending approximately 5 mm from said probe body, and is adapted and arranged to be inserted approximately 5 mm into the scalp of the fetus.

* * * * *